United States Patent
Leitner et al.

(10) Patent No.: US 8,355,773 B2
(45) Date of Patent: Jan. 15, 2013

(54) RECORDING LOCALIZATION DEVICE TOOL POSITIONAL PARAMETERS

(75) Inventors: François Leitner, Uriage (FR); Dirk Friedrich, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 2167 days.

(21) Appl. No.: 10/348,583

(22) Filed: Jan. 21, 2003

(65) Prior Publication Data

US 2004/0143178 A1 Jul. 22, 2004

(51) Int. Cl.
*A61B 17/00* (2006.01)

(52) U.S. Cl. ........................................ 600/424

(58) Field of Classification Search ............ 600/426, 600/424; 606/86, 87, 130
See application file for complete search history.

(56) References Cited

U.S. PATENT DOCUMENTS

| | | | |
|---|---|---|---|
| 2,990,765 A | 7/1961 | Winzenburg | |
| 4,963,903 A | 10/1990 | Cane | |
| 5,299,288 A * | 3/1994 | Glassman et al. | 700/245 |
| 5,769,861 A * | 6/1998 | Vilsmeier | 606/130 |
| 5,873,822 A | 2/1999 | Ferre et al. | |
| 6,122,541 A | 9/2000 | Cosman et al. | |
| 6,184,922 B1 | 2/2001 | Saito et al. | |
| 6,341,231 B1 | 1/2002 | Jakab et al. | |
| 6,385,475 B1 | 5/2002 | Schulz et al. | |
| 6,484,049 B1 | 11/2002 | Lin et al. | |
| 6,514,259 B2 * | 2/2003 | Picard et al. | 606/88 |
| 6,827,733 B2 | 12/2004 | Boneau | |
| 6,877,239 B2 * | 4/2005 | Leitner et al. | 33/512 |
| 6,920,347 B2 | 7/2005 | Simon et al. | |
| 2002/0087101 A1 * | 7/2002 | Barrick et al. | 600/587 |
| 2002/0183610 A1 | 12/2002 | Foley et al. | |
| 2004/0030245 A1 * | 2/2004 | Noble et al. | 600/426 |
| 2004/0106926 A1 * | 6/2004 | Leitner et al. | 606/87 |

FOREIGN PATENT DOCUMENTS

WO WO98/38908 9/1998

* cited by examiner

*Primary Examiner* — Parikha Mehta
(74) *Attorney, Agent, or Firm* — RatnerPrestia

(57) ABSTRACT

A localization device display method and apparatus for recording positional parameters associated with a tool being navigated with the localization device. The localization device monitors the position of a tool and automatically records positional parameters associated with the tool when the positional parameters conform to an area of interest and the tool is stable.

28 Claims, 3 Drawing Sheets

RECORDING LOCALIZATION DEVICE TOOL POSITIONAL PARAMETERS

FIELD OF THE INVENTION

The present invention relates to medical instruments and, more particularly, to a method and apparatus for recording positional parameters associated with a tool used during a surgical procedure that is tracked by a localization device.

BACKGROUND OF THE INVENTION

Localization devices have been developed to assist surgeons in performing surgical procedures. Markers are attached to bones that are observable by a stereoscopic camera system connected to a data processing system that records the positions of the markers in space to establish a coordinate reference system relative to each bone. Additional markers are attached to tools used during the surgical procedures. Typically, these markers are removable so that one marker can be used with multiple tools as needed during a procedure. By tracking the marker associated with a tool, positional parameters associated with the tool can be tracked in the coordinate reference systems of the bones. A monitor displays a representation of the bones and the position of the tools in the coordinate reference systems of the bones for use in guiding a surgeon during surgical procedures. A description of one particular localization device is described in U.S. Pat. No. 6,385,475 to Cinquin et al., incorporated fully herein by reference.

Surgical procedures performed using a localization device are typically carried out in a number of sequential steps. For example, to make a cut in a bone, initially, a number of steps are performed using the localization device in order to establish a coordinate reference system and to determine the precise angle and depth of the cut to be made in the bone. The localization device is then used in a first navigation step to guide a surgeon in the placement of a cutting jig, which contains a cutting guide used to guide a saw in a cutting plane defined by the cutting guide. A removable marker attached to the cutting jig allows the localization device to track the cutting jig to obtain information for use in performing the first navigation step. Once the cutting jig is in place, it is secured to the bone with pins. After the cutting jig is secured, the removable marker is removed from the cutting jig for later attachment to tools used in subsequent navigation steps.

Often, during a procedure, it is desirable to record positional parameters associated with a tool at the end of a navigation step for post operative analysis. For example, when making a cut in a bone, it is desirable to record the angle of the cutting plane defined by the cutting guide of a cutting jig and the distance of the cutting plane from a reference point on the bone to determine if the cutting jig was positioned properly or to compare the positional parameters of the cutting jig to the positional parameters of cutting jigs in similar procedures and their roles in the success or failure of a procedure. Ideally, when a surgeon finishes a navigation step, prior to the removal of the marker from the tool being navigated, the surgeon provides an indication to the localization device that this step of the procedure is over, e.g., by depressing a foot switch coupled to the localization device. The localization device then records the positional parameters associated with the tool. Sometimes, however, the surgeon removes the marker prior to indicating that this step of the procedure is over. Thus, since the marker is no longer associated with the tool, the positional parameters recorded by the localization device will not represent the actual positional parameters associated with the tool. Hence, the recorded positional parameters will be useless.

A surgeon's primary focus during a procedure is the successful completion of that particular procedure. Thus, steps that are not critical to the success of the operation may be seen as burdensome to the surgeon. Therefore, the surgeon may neglect to perform inconvenient tasks such as indicating that a navigation step is over prior to removal of the marker from the tool being navigated if it is not critical to the present procedure and the only reason for doing so is the accumulation of data for post operative analysis.

Accordingly, a convenient method is needed that ensures navigated tool positional parameters are accurately recorded.

SUMMARY OF THE INVENTION

The present invention provides a method and apparatus for accurately recording positional parameters associated with a tool that is navigated using a localization device. The aforementioned problems are overcome by automatically recording the positional parameters associated with the tool in the last stable position of the tool when the positional parameters are within a defined area of interest. By automatically recording the positional parameters during the last stable position of the tool, accurate positional parameters can be ascertained without additional input from a surgeon. Thus, navigated tool positional parameters may be recorded conveniently and accurately.

One aspect of the present invention is a method of recording tool positional parameters with a localization device. The method includes monitoring the position of a tool with the localization device and recording at least one positional parameter associated with the tool if a portion of the tool is moved less than a predetermined amount over a predetermined period of time.

Another aspect of the invention is a localization system for automatically recording positional parameters associated with a tool. The localization system includes sensors for tracking a marker associated with a tool and a computer coupled to the sensors for monitoring the position of the tool, calculating at least one positional parameter associated with the tool, and recording the at least one positional parameter when a portion of the tool is moved less than a predetermined amount over a predetermined period of time.

The steps of the method may be embodied in a computer readable medium or may form a system comprising means for performing the method steps.

BRIEF DESCRIPTION OF THE DRAWINGS

In the drawings, the same reference numerals are used to indicate the same elements.

DETAILED DESCRIPTION OF THE INVENTION

Figure 1:
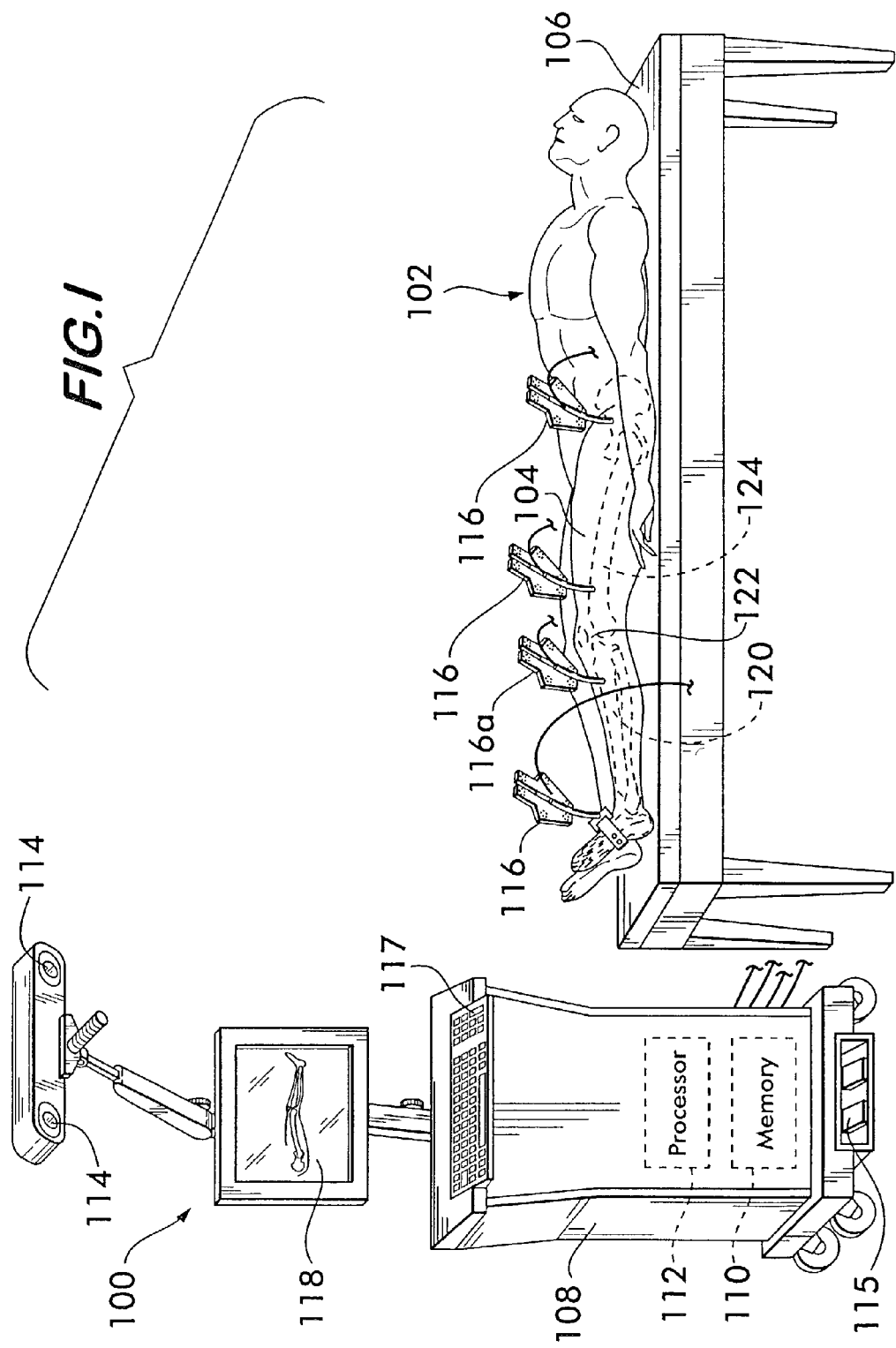
FIG. 1 is an illustration of a patient about to undergo a procedure utilizing a localization device in accordance with the present invention.

FIG. 1 depicts a localization device 100 in which the method of the present invention may be employed. In FIG. 1, a patient 102, who is to undergo a procedure, e.g., a Total Knee Arthroplasty (TKA) procedure on a leg 104, is illustrated schematically lying on an operating table 106. The localization device 100 includes a computer 108 loaded with software for surgical navigation, a memory 110, a processor 112, sensors 114, e.g., cameras, capable of detecting markers 116, foot pedals 115, a keyboard 117, and a monitor 118 for displaying surgical navigation information to a surgeon to guide the surgeon during the procedure. The sensors 114 are positioned above and laterally from the patient 102 so that the patient's leg 104 is in the field of view of the sensors 114. In general, the markers 116 are fixedly mounted on bones and surgical tools so that the localization device 100 can track the exact location and orientation of the bones and surgical tools to which they are mounted. A description of a suitable localization device 100 and method is found in U.S. Pat. No. 6,385,475 to Cinquin et al., having a common inventor and commonly assigned to the same entity as the present application, incorporated herein in full by reference.

For descriptive purposes, an exemplary embodiment of the present invention will be described in connection with the navigation of a cutting jig (see description of FIG. 3 below) for guiding a saw blade in the removal of a portion of a tibia 120 during one step of a TKA procedure. The TKA procedure involves replacing the damaged knee 122 by resurfacing the tibia 120 and femur 124 at the knee 122 with metal and/or plastic prostheses to form an artificial joint. The procedure involves sawing off the ends of the tibia 120 and femur 124 near the knee 122 very precisely to create surfaces of precise shape and location to accept the prostheses. Although the description of the present invention focuses on recording positional parameters associated with a cutting jig navigated by a localization device during a TKA procedure, it will be readily apparent to those skilled in the art that the present invention may be used with any number of surgical tools in any number of procedures.

Figure 2:
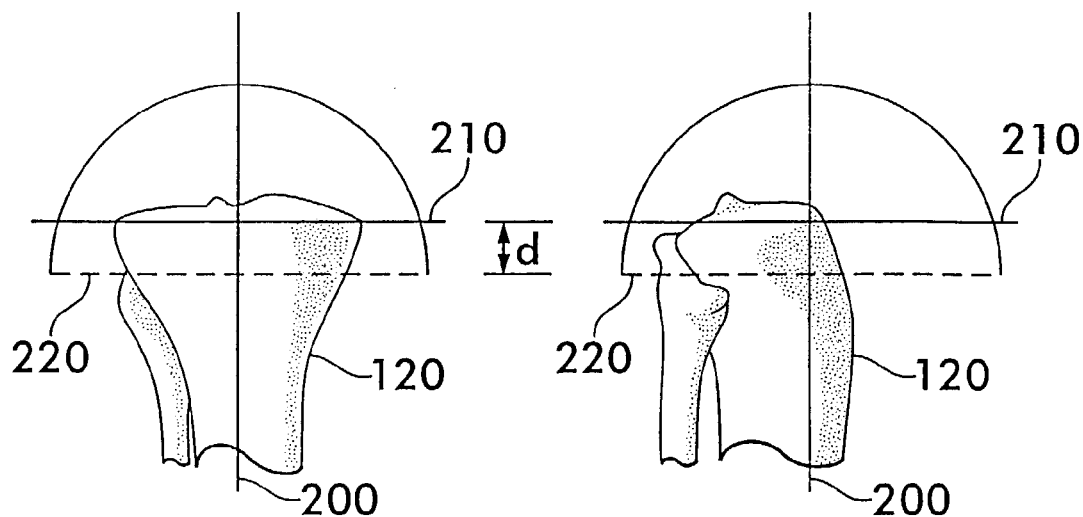
FIG. 2 is an illustration of a tibia represented by the localization device of FIG. 1 during a TKA procedure.

FIG. 2 illustrates front and side views of a tibia 102. The illustrated views are generated by the localization device 100 of FIG. 1 for display on the monitor 118 during a tibia cutting jig navigation step. Prior to the navigation step, the surgeon, using the localization device 100, acquires reference features associated with the tibia 120 in a known manner for use in the navigation. The reference features include a mechanical axis 200 of the tibia 120, a knee joint interline 210, and a desired cutting plane 220. The mechanical axis 200 of the tibia 120, which extends through the center of the knee and the center of the ankle, is determined using the localization device in a known manner. The knee joint interline 210, which represents a physical point of contact between the tibia 120 and the femur 124 (FIG. 1), may be determined by physically palpating one or more points on the knee joint interline 210 on the tibia 120 in a known manner using a pointer containing a marker being tracked by the localization device, which records the positions of the palpated points by detecting the position of the pointer relative to the markers fixedly mounted to the bones when the points are palpated. The desired cutting plane 220, which represents where the tibia 120 should be cut, is oriented such that the mechanical axis 210 of the tibia 120 is normal to the desired cutting plane 210 and the desired cutting plane is a predefined distance, d (e.g., 8 millimeters), from the knee joint interline 210 as measured along the mechanical axis 200 of the tibia 120. In one embodiment, the localization device receives the predefined distance from a surgeon through the keyboard 117 (FIG. 1).

Figure 3:
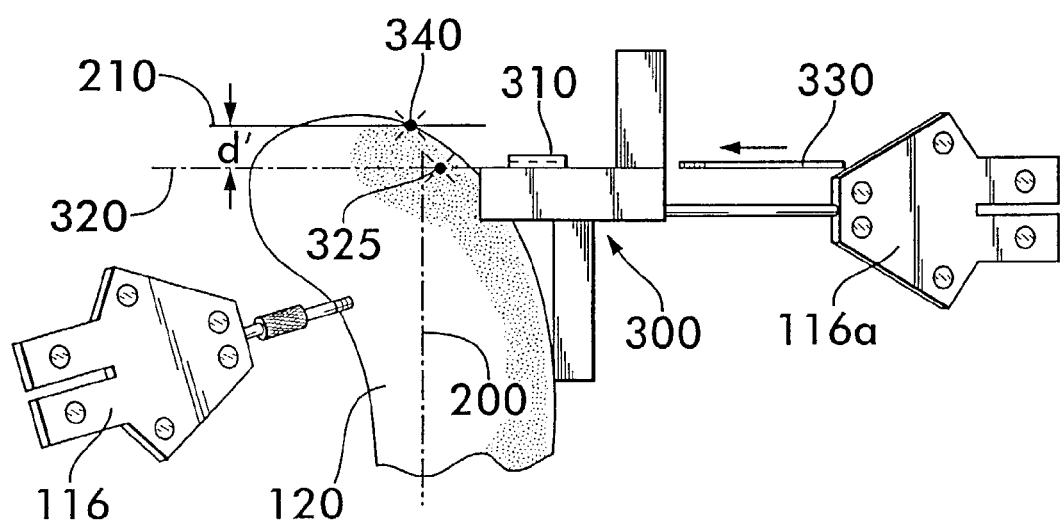
FIG. 3 is an illustration depicting positional parameters associated with a cutting jig used in a TKA procedure.

FIG. 3 depicts a cutting jig 300 positioned on the tibia 120. The cutting jig 300 contains a cutting guide 310 that defines a cutting plane 320 (represented by a line in FIG. 3) for guiding a cutting blade 330 of a saw (not shown). The cutting jig 300 is capable of receiving a marker 116a for tracking by the localization device 100 (FIG. 1). The marker 116a can be mounted on the cutting jig 300 in only one predetermined way and the localization device 100 is preprogrammed with data indicating the orientation and position of the cutting plane 320 relative to the marker 116a. Preferably, the localization device 100 is also preprogrammed with data indicating the position of a predefined point 325 on the cutting plane 320 relative to the marker 16a. By observing the marker 16a, the localization device 100 can determine the position and orientation of the cutting plane 320 of the cutting jig 300 and the position of the predefined point 325 relative to other points known to the localization device 110, e.g., a palpated point 340 on the knee joint interline 210 of the tibia 120 in the frame of reference of the tibia (the frame of reference being defined by the position of the tibial marker).

Positional parameters associated with the cutting jig 300 are developed by the localization device 100. In a preferred embodiment, the positional parameters are one or more parameters associated with the cutting jig 300 in one or more frames of reference for use in guiding a surgeon during the navigation of the cutting jig 300. In one embodiment, the positional parameters for the cutting jig 300 include an angular measurement and a linear measurement in the frame of reference of the tibia 120. The angular measurement represents an angle between the mechanical axis 200 of the tibia 120 and a vector normal to the cutting plane 320 of the cutting jig 300. In one preferred embodiment, the angular positional parameter is that the difference between the mechanical axis 200 or the tibia 120 and a vector normal to the cutting plane 320 of the cutting jig 300 is 3 degrees or less. The linear measurement represents the linear distance, d', of a vector component parallel to the mechanical axis 200 of the tibia 120 for a vector extending between a point on the cutting plane 320 and a point on the knee joint interline 210. In a preferred embodiment, the point on the cutting plane 320 is the predefined point 325, the point on the knee joint interline 210 is the palpated point 340, and the linear positional parameter is that the distance between the point on the cutting plane and the point on the knee joint interline is greater than 5 millimeters and less than 20 millimeters.

For post operative analysis, it is useful to record the positional parameters associated with the cutting jig 300 after it is secured to the tibia 120. Prior to the present invention, the positional parameters of the cutting jig 300 were recorded when the surgeon instructed the localization device 100 to proceed to the next step of the procedure, e.g., by depressing the foot pedal 115 (FIG. 1) coupled to the localization device 100. If the marker 116a attached to the cutting jig is removed prior to the surgeon's instruction to proceed, the positional parameters recorded by the localization device 100 will not accurately represent the positional parameters of the cutting jig.

Figure 4:
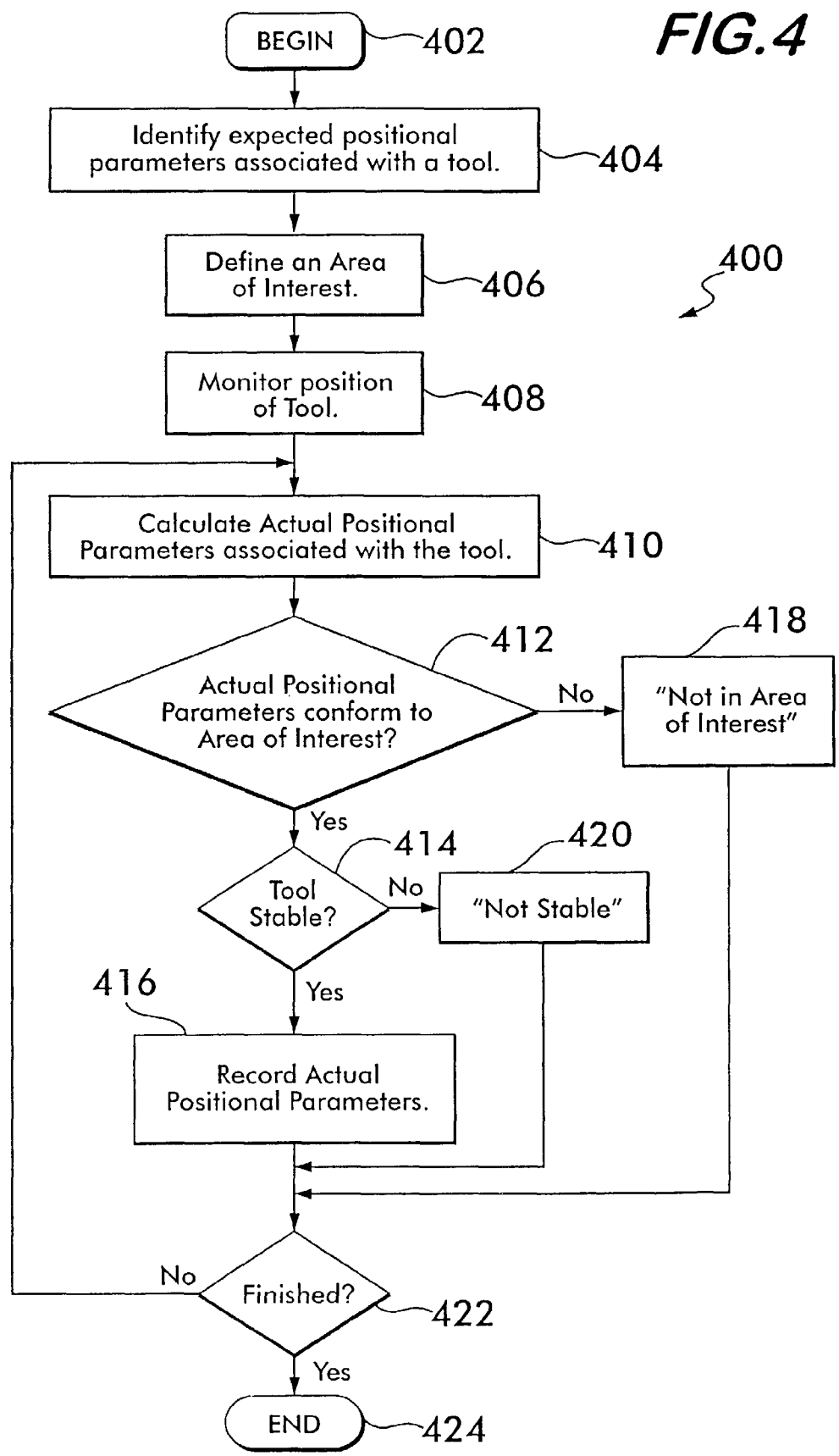
FIG. 4 is a flow chart depicting steps for automatically recording positional parameters associated with a tool being navigated utilizing a localization device in accordance with the present invention.

FIG. 4 depicts a flow chart 400 for a preferred method for automatically recording accurate positional parameters associated with a navigated surgical tool (hereinafter the "tool"), e.g. the cutting jig 300 in the exemplary embodiment. At block 402, the method begins. In a preferred embodiment, the method begins when invoked by the localization device 100 during one or more specific portions of a procedure. For example, the localization device 100 may invoke the method during the navigation of a cutting jig 300 (FIG. 3) used to guide a saw blade 330 in the removal of a portion of a tibia 120 during a TKA procedure.

At block 404, expected positional parameters associated with the tool are identified. The expected positional parameters represent ideal parameters associated with a properly navigated tool. For the exemplary cutting jig 300 depicted in FIG. 3, in accordance with one embodiment, the cutting jig 300 is properly navigated when the cutting plane 320 is perpendicular to the mechanical axis 200 of the tibia 120 and the cutting plane 320 is a predefined distance from the knee joint interline 210. Thus, in this embodiment, the expected positional parameters associated with the cutting jig 300 include an angular component and a spatial component.

The angular component is an angle between the mechanical axis 200 of the tibia 120 and a vector normal to the expected cutting plane 220 (FIG. 2), which, preferably, is approximately zero degrees. Preferably, the angular component is represented using two angular parameters about two axes, respectively, e.g., a first axis perpendicular to the mechanical axis 200 and parallel to the knee joint interline 210 and a second axis perpendicular to both the mechanical axis 200 and the knee joint interline 210. As will be readily apparent to those skilled in the art, the orientation of a plane can be expressed using two angles since the rotation of the plane about an axis normal to the plane, e.g., the mechanical axis 200, is irrelevant. The spatial component is a predefined spatial parameter representing a distance, d (FIG. 2), e.g., approximately 8 millimeters, from the knee joint interline 210 in a direction parallel to the mechanical axis 200 of the tibia 120. It will be noted by those skilled in the art that, although in the present example the expected positional parameters can be represented by two angular parameters and one spatial parameter, the expected positional parameters may include essentially any number and type of parameters.

At block 406, an area of interest is defined. The defined area of interest specifies the tolerances for the expected positional parameters identified in block 404. Preferably, a separate tolerance value is specified for each identified expected positional parameter. For the exemplary cutting jig 300, the expected positional parameters at block 404 were represented in terms of one spatial parameter and two angular parameters. In this embodiment, the spatial parameter, which is a predefined distance d from the knee joint interline 210, includes a range of distances for this parameter, e.g., from 5 millimeters to 20 millimeters. Likewise, the two angular parameters, which are expressed in terms of an angular relationship, e.g., 0 degrees to a vector normal to the cutting plane, may include a range of angles for these parameters, e.g., up to 3 degrees for each of the angular parameters.

At block 408, the position of the tool is monitored by the localization device 100. For the exemplary cutting jig 300, the position of the cutting jig 300 is monitored by tracking the marker 116a attached to the cutting jig 300 in a frame of reference for the tibia 120. In one embodiment, as described above, the localization device 100 is preprogrammed with instructions that define the orientation of the cutting plane 320 of the cutting jig 300 and further define a, point 325 on that cutting plane 320, e.g., a point in space one centimeter from the leading edge of the cutting guide 310 of the cutting jig 300. Thus, the position of the cutting jig 300 may be expressed in terms of the orientation of the cutting plane 320 and in terms of the location of the predefined point 325 in space in the tibia's frame of reference. In this embodiment, the orientation of the cutting plane 320 is represented using two angles and the location of the predefined point 325 is represented using a three dimensional coordinate system. The position of the cutting jig 300 is continuously monitored throughout the rest of the steps of flow chart 400.

At block 410, actual positional parameters associated with the tool are calculated. For the exemplary cutting jig 300, each of the actual positional parameters corresponds to one of the expected positional parameters identified at block 404. Thus, the actual positional parameters associated with the cutting jig 300 include two angular parameters and a spatial parameter. To determine the angular parameters, the angles between the mechanical axis and a vector normal to the cutting plane 320 of the cutting jig 300 about a first axis and a second axis are calculated. Preferably, the localization device 100 determines the angular parameters by calculating a vector normal to the cutting plane 320 in a known manner using the tool positions monitored at block 408 and comparing the calculated value to the mechanical axis 200 of the tibia 120. To determine the spatial parameter, the vector component parallel to the mechanical axis 200 of the tibia 120 is calculated for a vector that extends between the predefined point 325 on the cutting plane 320 and the palpated point 340 on the knee joint interline 210. Preferably, the localization device 100 determines the spatial parameter by calculating the vector component parallel to the mechanical axis 200 of the tibia 120 for a vector extending between the predefined point 325 on the cutting plane 320 and the palpated point 340 on the knee joint interline 210.

At block 412, the actual positional parameters of the tool calculated at block 410 are compared to the expected positional parameters identified at block 404 to determine if they conform to the area of interest defined at block 406. The localization device 100 determines if the actual positional parameters are within the area of interest by comparing them to the expected positional parameters to see if each one of the actual positional parameters conform to the area of interest surrounding the corresponding expected positional parameters. If every one of the actual positional parameters conform to the area of interest surrounding the corresponding expected positional parameters, the actual positional parameters conform to the area of interest and processing proceeds to block 414. Otherwise, if the actual positional parameters do not conform, an indicator is generated at block 418, such as a prompt to display a message indicating that the actual positional parameters are "Not in Area of Interest" for display on a monitor 118 (FIG. 1) of the localization device 100.

At block 414, the stability of the tool is determined. In a preferred embodiment, the tool is deemed stable if a portion of the tool is stationary for a specified period of time, e.g., greater than about 3 seconds and, preferably, greater than about 6 seconds. Preferably, the tool is stationary if the tool moves less than a predefined distance, e.g., 0.5 millimeters, in any spatial direction and rotates less than a predefined amount, e.g., 0.5 degrees, in any angular direction. If the tool is stable, processing proceeds to block 416. Otherwise, if the tool is not stable, an indicator is generated at block 420, such as a prompt to display a message indicating that the cutting jig is "Not Stable" for display on the monitor 118 (FIG. 1) of the localization device 100. For the exemplary cutting jig 300, the localization device 100 determines if the cutting jig 300 is stable by tracking the position of the cutting jig 300 as monitored at block 408 for the specified period of time. If the orientation of the cutting plane 320 represented using two angles at block 308 rotates less than the predefined amount in each angular direction and the location of the predefined point 325 represented using a three dimensional coordinate system moves less than the predefined distance in any direction for the predefined period of time, the cutting jig 300 is stable and processing proceeds to block 416. Otherwise, processing proceeds to block 420. For other surgical tools, such as a pointer, it is contemplated that the surgical tool may be considered stable if a specific portion of the surgical tool, e.g., the tip of the pointer, moves less than a predetermined amount during a predetermined period of time since stability in the orientation of certain surgical tools, e.g., a pointer, is typically not as crucial as stability in a portion of the tool, e.g., the pointer tip.

At block 416, the positional parameters associated with the tool, e.g., the cutting jig 300, are recorded. The localization device may record the positional parameters in a conventional memory 110 (FIG. 1). In one embodiment, only the positional parameters for the last stable position of the tool are recorded with positional parameters for previous stable positions of the tool, if any, being overwritten by positional parameters for more recent stable positions. In an alternative embodiment, positional parameters for each stable position are recorded.

At block 422, a determination is made as to whether the specific portion of the procedure in which the method was invoked in block 402 is finished. In a preferred embodiment, the surgeon indicates when that portion of the procedure is finished, e.g., by depressing a foot pedal. If the portion of the procedure is finished, processing proceeds to block 424. Otherwise, if the portion of the procedure is not finished, processing proceeds back to block 410 so that the device can continue to collect and record positional parameters as described in connection with steps 412 to 420.

In one embodiment, the surgeon may still manually prompt the localization device to record positional parameters. For example, the surgeon may depress a foot pedal 115 (FIG. 1) or a key of a keyboard 117 (FIG. 1) when the surgeon desires to record positional parameters associated with the cutting jig. The positional parameters recorded upon prompting by the surgeon may be stored in addition to positional parameters automatically recorded in accordance with the present invention or may replace one or more automatically recorded positional parameters. The surgeon may desire to record positional parameters when the surgeon believes that the cutting jig is properly positioned, rather than rely solely on the automated recording described hereinabove and in connection with FIG. 4. The positional parameters recorded at the surgeon's prompting may be useful during post operative analysis for comparison to automatically recorded positional parameters obtained through the steps of blocks 410-422 for verification of the accuracy of the automatically recorded positional parameters.

Although the present invention has been described in terms of recording the last stable position of a cutting jig during a cutrting jig navigation step of a TKA procedure, it will be readily apparent to those skilled in the art that the present invention may be used to record the position of essentially any tool during steps of essentially any procedure in which a localization device is employed. For example, the present invention may be used to record the last stable position of a check blade inserted into a cut within a bone during a wedge resection procedure such as described in U.S. patent application Ser. No. 10/307,594 entitled OSTEOTOMY PROCEDURE, filed on Dec. 2, 2002.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for recording positional parameters of a tool navigated using a localization device during a procedure, the method comprising the steps of:

monitoring at least one positional parameter of a tool with said localization device;

displaying information indicative of said at least one positional parameter of said tool;

determining with the localization device whether said tool is stable for a predetermined period of time during the procedure; and responsive to said tool being stable for the predetermined period of time as determined by the localization device, storing with the localization device said at least one positional parameter of said tool at an instant in time at an end of said predetermined period of time for a period of time extending beyond an end of said procedure.

2. The method of claim 1, wherein said tool is capable of receiving a marker for tracking by the localization device to enable monitoring of said at least one positional parameter of said tool.

3. The method of claim 1, further comprising the steps of: defining a range of interest for said at least one positional parameter; and determining if said at least one positional parameter conforms to said range of interest, wherein said at least one positional parameters is recorded only if said at least one positional parameter conforms to said range of interest.

4. The method of claim 3, wherein said range of interest defines tolerances for said at least one positional parameter.

5. The method of claim 3, further comprising the step of: generating a first indicator if said at least one positional parameter does not conform with said range of interest.

6. The method of claim 5, further comprising the step of: generating a second indicator if said tool does not move less than said predetermined amount over said predetermined period of time.

7. The method of claim 1, wherein said predetermined period of time is greater than about 3 seconds.

8. The method of claim 1, wherein said tool is stable when said tool moves less than about 0.5 millimeters in any direction.

9. The method of claim 1, wherein said tool is stable when said tool moves less than 0.5 millimeters in any spatial direction and less than 0.5 degrees in any angular direction.

10. The method of claim 1, wherein the procedure is a surgical procedure.

11. The method of claim 10, wherein said surgical procedure is performed on a bone having a mechanical axis and said tool is a cutting jig being navigated by the localization device for mounting on the bone.

12. The method of claim 11, wherein said cutting jig defines an associated cutting plane and wherein said at least one positional parameter comprises at least two positional parameters including (a) an angle between a vector normal to the cutting plane and the mechanical axis of the bone and (b) a distance between a point on the bone and a point on the cutting plane.

13. The method of claim 12, wherein said angle is less than about 3 degrees and said distance is between about 5 millimeters and 20 millimeters.

14. A method for recording positional parameters associated with a tool navigated using a localization device, said localization device used to perform an osteotomy procedure on a bone, said method comprising the steps of:

identifying at least one expected positional parameter associated with the tool;

defining a range of interest for said at least one expected positional parameter with the localization device;

monitoring the position of the tool with the localization device;

calculating with the localization device at least one actual positional parameter associated with the tool based on the monitored position of the tool;

displaying information indicative of the position of said tool;

determining with the localization device whether said at least one actual positional parameter conforms to the range of interest;

determining with the localization device whether said tool is stable for a predetermined period of time during the procedure while said at least one actual positional parameter conforms to the range of interest; and responsive to said at least one actual positional parameter conforming to the range of interest as determined by the localization device and said tool being stable for the predetermined period of time while said at least one actual positional parameter conforms to the range of interest as determined by the localization device, storing with the localization device said at least one actual positional parameter at an instant of time at an end of said predetermined period of time for a period of time extending beyond an end of said osteotomy procedure.

15. The method of claim 14, further comprising at least the step of:

generating a first indicator if said at least one positional parameter does not conform to said range of interest.

16. The method of claim 15, further comprising the step of: generating a second indicator if said tool is stable for said predetermined period of time.

17. The method of claim 14, wherein said predetermined period of time is greater than about 3 seconds.

18. The method of claim 14, wherein said tool is stable when said tool moves less than about 0.5 millimeters in any direction.

19. The method of claim 14, wherein said tool is stable when said tool moves less than about 0.5 millimeters in any spatial direction and about 0.5 degrees in any angular direction.

20. The method of claim 14, wherein the tool is a cutting jig bearing a marker; and wherein said monitoring step comprises observing said marker with the localization device and determining the position of the cutting jig based on the observation.

21. A localization system comprising:

sensors for tracking a marker associated with a tool during a procedure; and a computer coupled to said sensors for monitoring the position of said tool, the computer programmed to:

calculate at least one positional parameter of said tool based on the monitored position, determine whether said tool is stable for a predetermined period of time during the procedure; and store the at least one calculated positional parameter at an instant in time for a period of time extending beyond an end of said osteotomy procedure responsive to said tool being stable for a predetermined period of time, as determined by the computer.

22. The system of claim 21, wherein said computer further identifies a range of interest associated with at least one expected positional parameter and only records the at least one calculated positional parameter if said at least one calculated positional parameter conforms to said range of interest.

23. The system of claim 21, further comprising at least:

a monitor coupled to said computer, wherein said computer causes said monitor to display a first message when said at least one calculated positional parameter does not conform to said range of interest.

24. The system of claim 23, wherein said computer causes said monitor to display a second message when said tool is stable over a predetermined period of time.

25. A computer program product for recording tool positions with a localization device during a procedure, said computer program product comprising:

computer readable program code embodied in a non-transitory computer readable medium, the computer readable program code comprising at least:

computer readable program code for monitoring at least one positional parameter of a tool with said localization device during a procedure;

computer readable program code for determining with the localization device whether said tool is stable for a predetermined period of time during the procedure; and computer readable program code for responsive to said tool being stable for the predetermined period of time as determined by the localization device, storing with the localization device said at least one positional parameter associated with said tool at an instant in time at an end of said predetermined period for a period of time extending beyond an end of said procedure.

26. The product of claim 25, further comprising:

computer readable program code for defining a range of interest for said at least one positional parameter; and computer readable program code for determining if said at least one positional parameter conforms to said range of interest, wherein said at least one positional parameters is recorded only if said at least one positional parameter conforms to said range of interest.

27. A system for recording tool positions with a localization device, said system comprising:

means for monitoring at least one positional parameter of a tool with said localization device during a procedure;

means for determining whether said tool is stable for a predetermined period of time during the procedure; and means for, responsive to said tool being stable for the predetermined period of time as determined by the determining means, storing said positional parameter at an end of said predetermined period of time for a period of time extending beyond a end of said procedure.

28. The system of claim 27, further comprising the steps of:

means for defining a range of interest for said at least one positional parameter; and means for determining if said at least one positional parameter conforms to said range of interest, wherein said at least one positional parameter is recorded only if said at least one positional parameter conforms to said range of interest.

* * * * *